US008568344B2

(12) United States Patent
Ferguson et al.

(10) Patent No.: US 8,568,344 B2
(45) Date of Patent: Oct. 29, 2013

(54) TORSO ASSIST ORTHOTIC DEVICE (71) Applicants: Daniel L. Ferguson, Appleton, WI (US); Lowell Mick N. Batton, Neenah, WI (US)

(72) Inventors: Daniel L. Ferguson, Appleton, WI (US); Lowell Mick N. Batton, Neenah, WI (US)

(73) Assignee: Applied Neural Mechanics, LLC, Appleton, WI (US)

(*) Notice: Subject to any disclaimer, the term of this patent is extended or adjusted under 35 U.S.C. 154(b) by 0 days.

(21) Appl. No.: 13/742,979

(22) Filed: Jan. 16, 2013

(65) Prior Publication Data

US 2013/0131560 A1 May 23, 2013

Related U.S. Application Data (63) Continuation-in-part of application No. 12/904,801, filed on Oct. 14, 2010, now abandoned.

(60) Provisional application No. 61/254,287, filed on Oct. 23, 2009.

(51) Int. Cl.
*A61F 5/00* (2006.01)

(52) U.S. Cl.
USPC ................................. 602/16; 602/19

(58) Field of Classification Search
USPC .............................. 602/5, 16, 19–28; 128/882
See application file for complete search history.

(56) References Cited

U.S. PATENT DOCUMENTS

| 4,481,941 A | 11/1984 | Rolfes |
| 7,803,127 B2 | 9/2010 | Giesen |
| 2005/0130815 A1 | 6/2005 | Abdoli-Eramaki |

FOREIGN PATENT DOCUMENTS

DE 19652416 A1 6/1998

*Primary Examiner* — Michael A. Brown
(74) *Attorney, Agent, or Firm* — Nicholas A. Kees; Godfrey & Kahn, S.C.

(57) ABSTRACT

A torso assist orthotic device configured to be worn by a user requiring assistance in holding his torso in a vertical position and returning the his torso to a vertical position from a forward bent over position. The torso assist orthotic device includes an upper body engaging portion that is open in the front in the abdominal and pelvic areas. A lower body engaging portion is custom formed to the wearer's lower extremities. A hinged connection at each side has a spring assist device in engagement. The spring assist device is selectively disengagable, such that when the spring assist device is engaged, the spring assist device provides resistance to forward movement of the user's torso and urges the user's torso back into alignment with the user's lower body. The spring assist device includes a self-latching spring engagement/disengagement device.

11 Claims, 12 Drawing Sheets

FIG. 19

TORSO ASSIST ORTHOTIC DEVICE

FIELD OF THE INVENTION

This invention relates to orthotic devices, and in particular to devices intended to assist patients who have difficulty standing and walking erect, including patients with camptocormia.

BACKGROUND

Certain patients have difficulty maintaining an upright posture. Particularly, camptocormia, a syndrome which is increasingly associated with Parkinson's Disease, causes patients to exhibit a severe, bent over posture when walking, standing or sitting. Camptocormia patients exhibit a characteristic forward and lateral lean when both standing and sitting. There is currently no recognized medical treatment or orthopedic device to mitigate this degenerative condition, permitting movement only in the saggital plane, while restricting movement in the coronal and axial planes.

U.S. Pat. No. 7,803,127, to Giesen, describes a device that is adjustable to accommodate different body sizes, the device shown in this reference provides insufficient support for handicapped people like those with camptocormia. Giesen's device intentionally permits movement in all three orthotic planes and specifically provides for lateral torso and thigh movements which are antithetical to supporting camptocormia patients, who have a tendency to fall without lateral support.

This invention relates to improvements to the apparatus described above and to solutions to some of the problems raised or not solved thereby.

SUMMARY OF THE INVENTION

According to the present invention, a torso assist orthotic device (TAO) is designed to support the torso using a pelvic girdle or band, and chest support, while transferring the associated forces through stiff torsion springs to the legs with thigh cuffs. Each of these components should be custom-molded to fit the individual patient but it is anticipated that versions or embodiments with adjustment features may be provided in standard sizes so that TAOs according to the present disclosure may be more readily available and adaptable to users at a variety of price points.

Fitted with a TAO according to the invention, when a standing patient desires to bend over, all that's required is to lean forward and relax. Individually-sized (or adjusted) torsion springs will preferably match the torso weight of the patient so that the effect of gravity on the torso is essentially counterbalanced. Once the task in the bent over position is completed, the patient is free to resume an erect position with only minimal muscle effort. Alternatively, it is anticipated that the assist provided by the TAO may be adjusted to match the muscular capabilities of the user. A patient may have some muscular strength to perform some of the lifting of the weight of their own torso and may only require a lesser assistance from the TAO. Other patients or users may have lost all or substantially all of their muscular ability to raise their trunk and may require a TAO to be able to assist in moving substantially all of the weight of their torso to an upright position.

More specifically, the invention provides a torso assist orthotic device configured to be worn by a user requiring assistance in holding the torso in a vertical position and returning the torso to a vertical position from a forward bent over position. According to the invention, the torso assist orthotic device includes an upper body engaging portion that is open in the front in the abdominal and pelvic areas. A lower body engaging portion is custom formed to the wearer's lower extremities. There is a hinged connection between the upper and lower body engaging portions, and a spring assist device mounted at and engaging the hinged connection. The spring assist device is selectively disengagable, such that when the spring assist device is engaged, the spring assist device provides resistance to forward movement of the user's torso and urges the user's torso back into alignment with the user's lower body. When the spring assist device is disengaged, the spring assist device provides no resistance to forward movement of the user's torso. The spring assist device includes a self-latching spring engagement/disengagement device.

The spring assist device also includes a forward stop to prevent the upper body engaging portion from going forward past approximately ninety degrees with regard to the lower body engaging portion, and a rearward stop to prevent the upper body engaging portion from going rearward past being generally in line with the lower body engaging portion. A spring is selected so as to match the weight of the user's torso, so that the spring assist device will essentially counterbalance the weight of the user's torso, and aid the return of the user's torso to a vertical position with minimal effort by the user, while employing minimal preload only as needed so as to minimally impede walking by minimizing pressure on the lower body engaging portion when walking.

Other objects and advantages of the invention will become apparent hereinafter.

BRIEF DESCRIPTION OF THE DRAWINGS

The accompanying drawing figures, which are incorporated in and constitute a part of the description, illustrate several aspects of the invention and together with the description, serve to explain the principles of the invention. A brief description of the figures is as follows.

DETAILED DESCRIPTION

Figure 1:
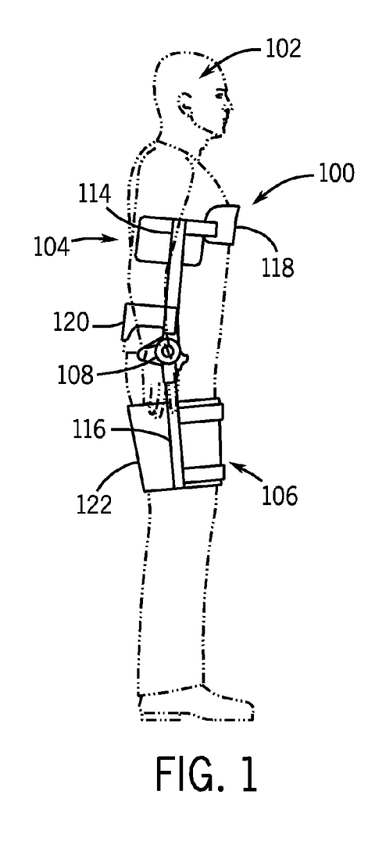
FIG. 1 is a side view of one embodiment of an orthotic device according to the invention showing a patient in an upright position.
Figure 2:
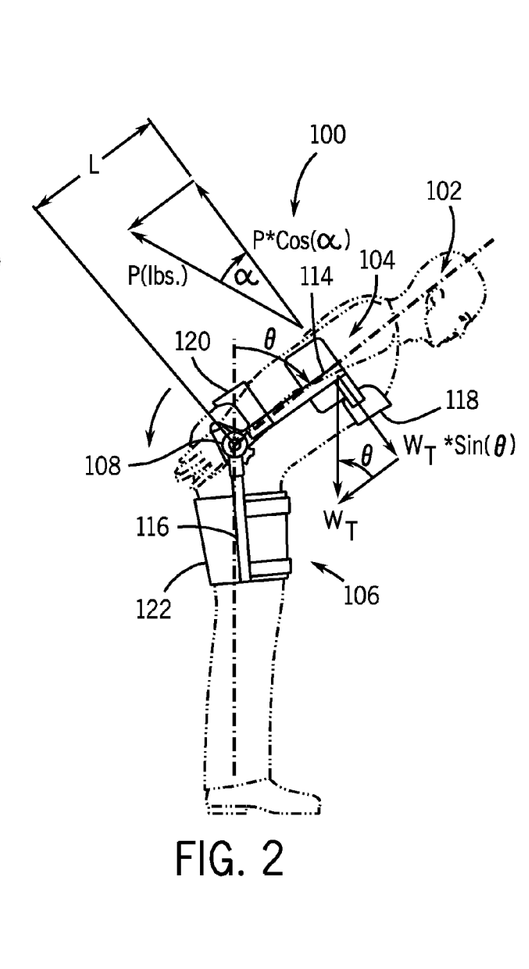
FIG. 2 is another side view of the orthotic device of FIG. 1 showing the patient in a bent-over position for determining the torsion spring rate needed to provide sufficient counterbalance torque for that specific patient.
Figure 3:
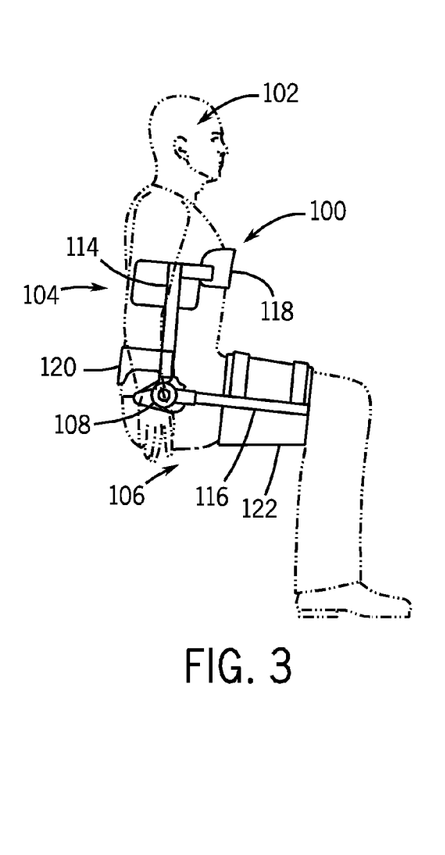
FIG. 3 is another side view of the orthotic device of FIG. 1 showing the patient in a seated position.

FIGS. 1 through 3 show one embodiment of a torso assist orthotic device (TAO) according to the present disclosure and will be referred to in the description as an illustrative and non-limiting example. Applicants anticipate that various options and alternatives will be apparent and it is not intended limit the present disclosure in any way. TAO 100 is illustrated as being worn or used by a user or patient 102 that requires assistance in holding his or her torso in a vertical position, and in returning the torso to a vertical position from a forward bent over position.

In general terms, the TAO 100 includes an upper body engaging portion 104 and a lower body engaging portion 106. In the embodiment shown, the upper body engaging portion 104 includes a chest support 118 attached to upper arms 114 and positioned in front of the patient, and a pelvic band 120, also attached to the upper arms 114, and wrapped around the patient's lower back near the top of the patient's sacrum, which thus provides back support. The chest support 118 is custom formed or molded to a particular patient's form, so as to ensure that males and females are properly supported in comfort. Similarly, in this embodiment, the lower body engaging portion 106 includes lower arms 116, attached to the patient's thighs with thigh cuffs 122.

Each of the body engaging portions is, in general, custom formed to the portion of the body to be engaged. That is, the upper body engaging portion 104 includes parts that are generally molded to the appropriate portion of the patient's back and chest, and the lower body engaging portion 106 includes parts that are generally molded to the appropriate portion or portions of the patient's lower body, or legs.

Figure 4:
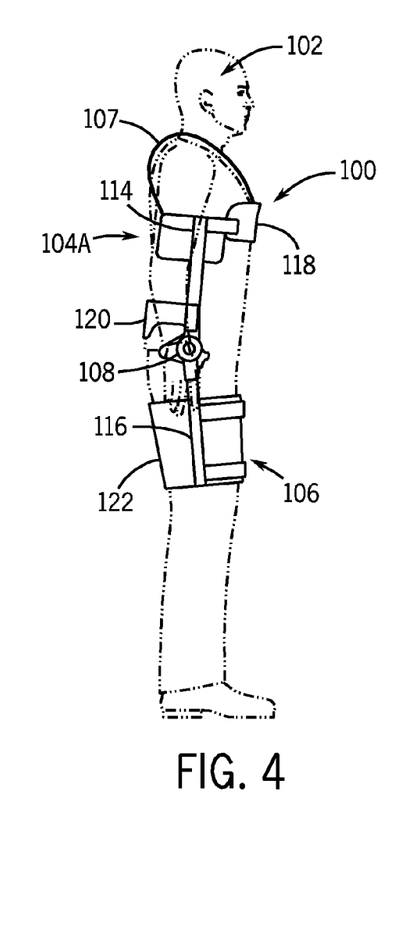
FIG. 4 is a side view of an alternative embodiment of an orthotic device in accordance with the invention showing a patient in an upright position.
Figure 5:
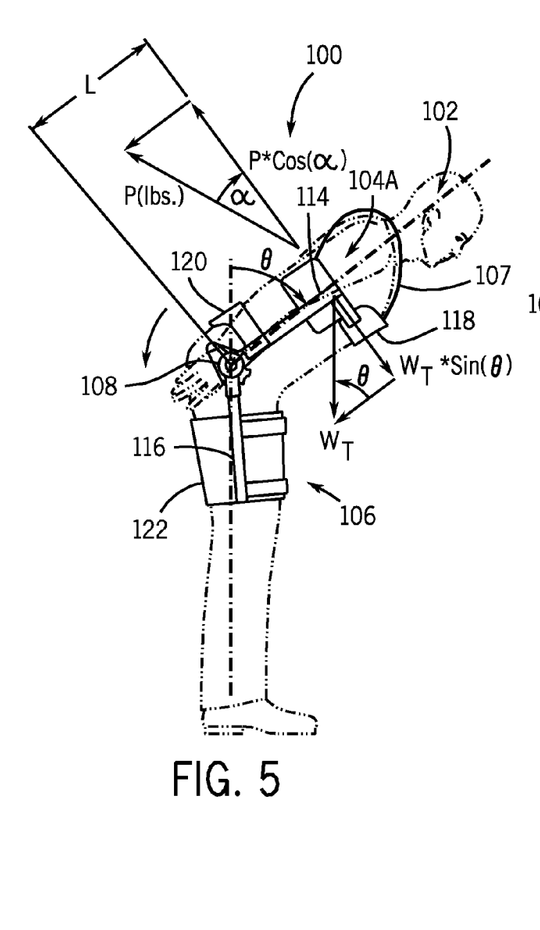
FIG. 5 is another side view of the orthotic device of FIG. 4 showing the patient in a bent-over position for determining the torsion spring rate needed to provide sufficient counterbalance torque for that specific patient.
Figure 6:
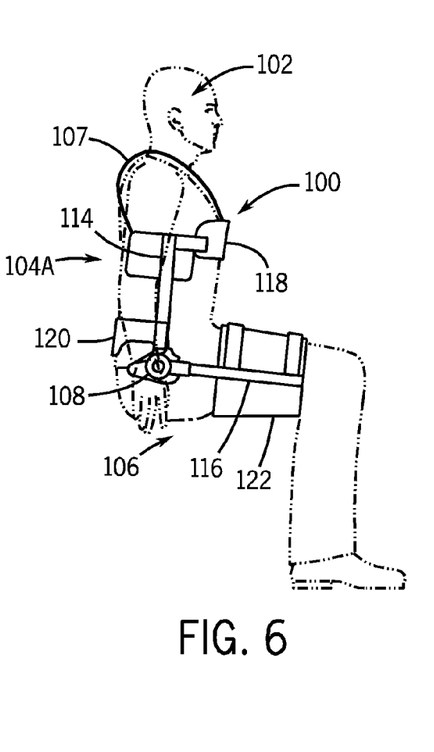
FIG. 6 is another side view of the orthotic device of FIG. 4 showing the patient in a seated position.

FIGS. 4-6 show an alternative configuration of the upper body engaging portion 104A, which includes shoulder straps 107, connected to the upper body engaging portion and extending over the patient's shoulders, which may optionally be used to limit vertical "migration" of the TAO device 100.

Figure 7:
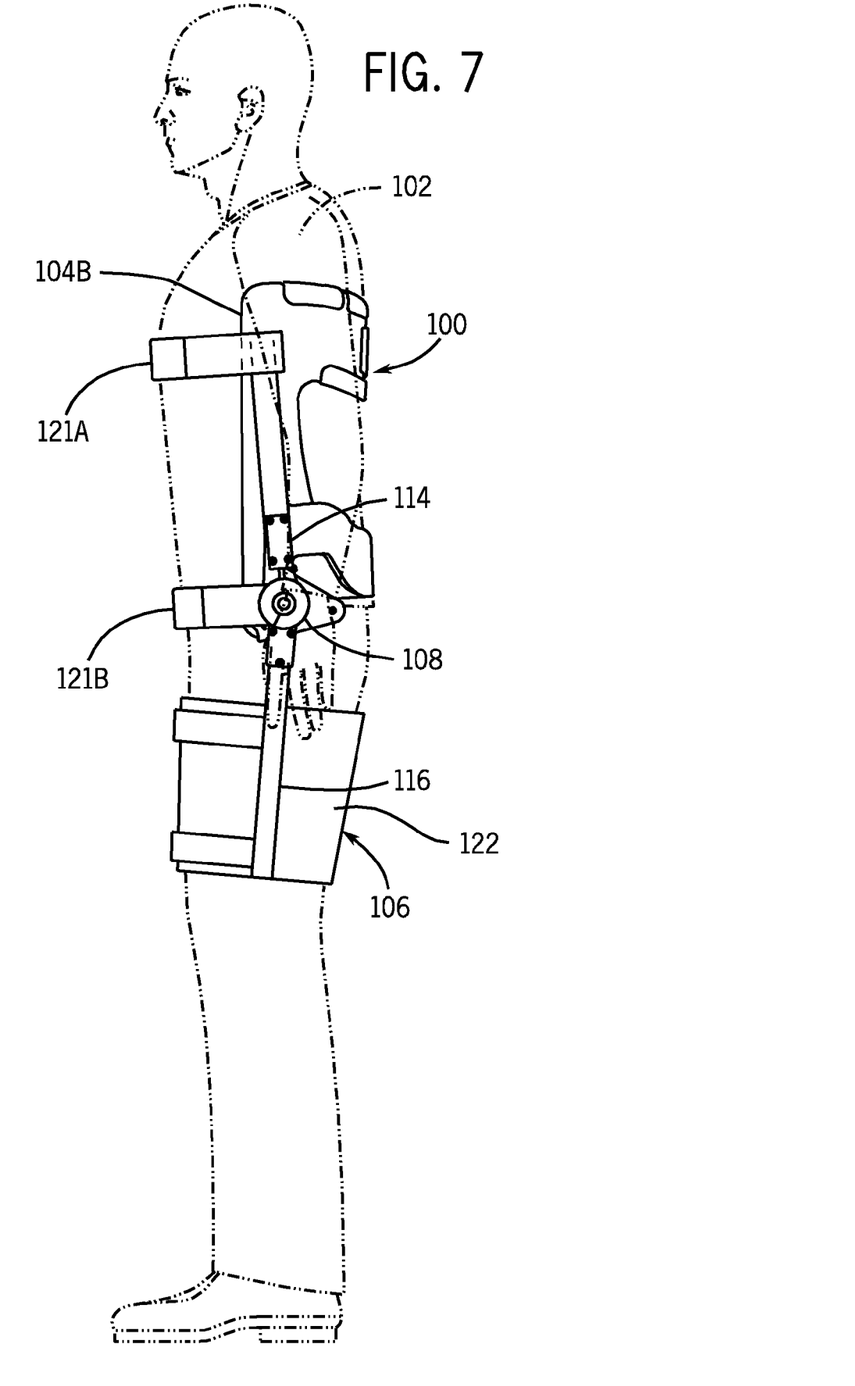
FIG. 7 is a side view of an orthotic device constructed according to another embodiment of the invention and applied to the body of a patient, and shown in an upright position.
Figure 8:
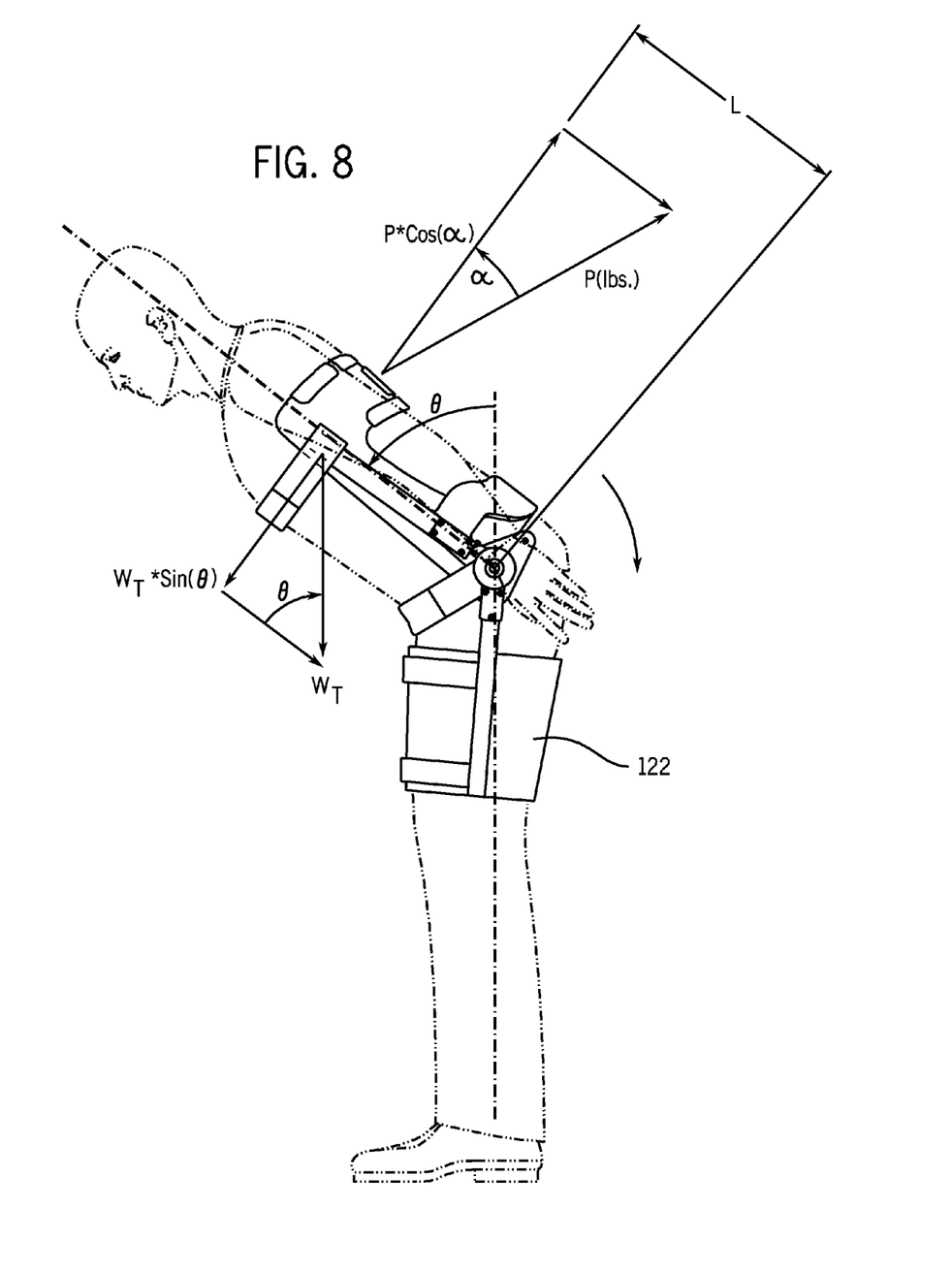
FIG. 8 is a side view of the patient shown in FIG. 7, in a position for determining the torsion spring rate needed to provide sufficient counterbalance torque for that specific patient.
Figure 9:
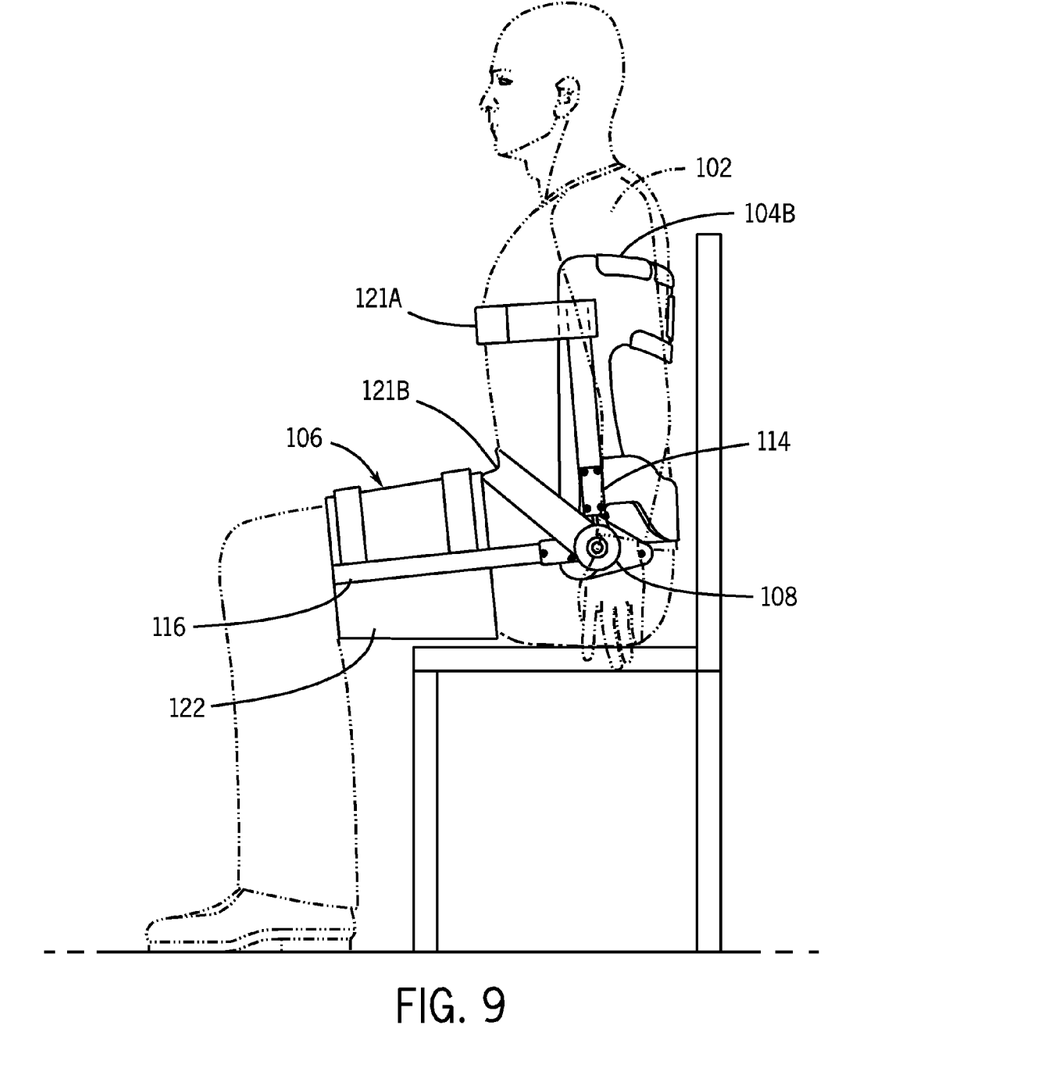
FIG. 9 is a side view of the patient shown in FIG. 7, wearing the orthotic device in a seated position.
Figure 10:
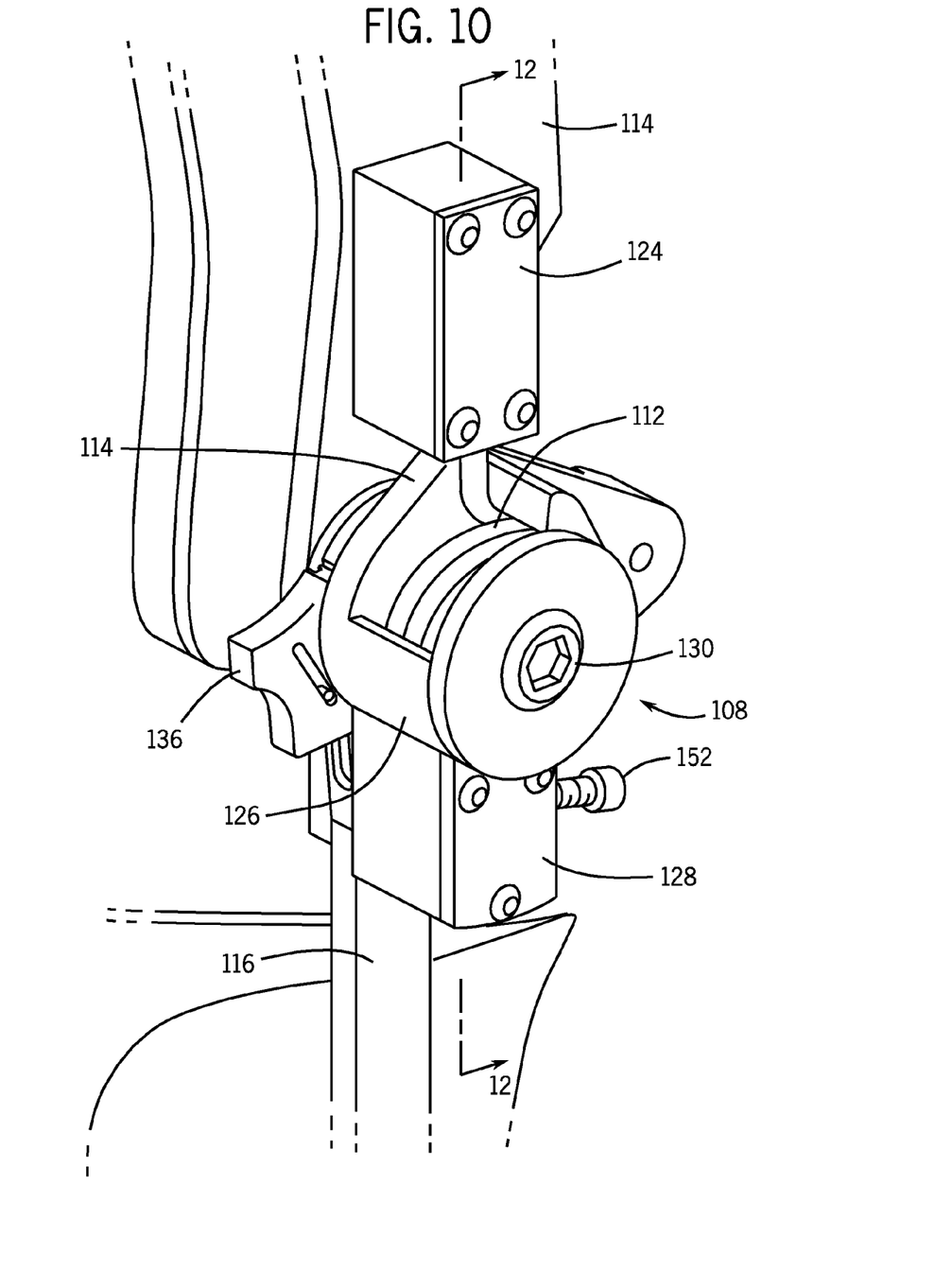
FIG. 10 is an enlarged isometric view of a hip joint which forms part of an orthotic device constructed according to a preferred embodiment of the invention.

FIGS. 7 through 9 illustrate another embodiment of a TAO 100 in accordance with the invention. In the embodiment shown, the upper body engaging portion 104B includes a larger back support 105, and two support straps, an upper strap 121A across the patient's chest, and lower strap 121B across the front of the abdomen of the patient, each of the straps being connected to the back support. The support straps 121A and 121B are adjustable to allow a semi-custom fit of the TAO 100. This embodiment may be considered not as desirable as the first two embodiments, as the support strap arrangement may not provide comfort as much as that provided by the molded chest support 118.

In all embodiments of the invention, a pair of hinged connections or hinge assemblies or mechanical hip joints 108 are provided between the upper body engaging portion 104 and the lower body engaging portion 106, that is, one hinged connection 108 is mounted to each side of the TAO 100. The inventors have found that certain commercially available hip joints work well for this use including, for example, a member of the PS200 series or PL200 series from the Center for Orthotics Design, or Model Numbers 028054 and 027404 from The Fillauer Companies. Other hip joint assemblies may be employed if the essential functions of the invention as identified herein are provided.

According to the invention, each hinged connection 108 comprises a spring assist device, providing assistance to the patient 102 by applying spring force to the upper body engaging portion 104, and thereby decreasing the force the patient must generate to change the alignment of his upper and lower body. In the embodiment shown, the hinged connection 108 includes a torsion spring 112 selected to match the weight of the user's torso so that the spring assist device will essentially render the user's torso substantially weightless, that is, the spring assist device will essentially counteract the weight of the user's torso, and thus aid the return of the user's torso to a vertical position with minimal effort by the user. The hinged connection 108 is selectively disengagable, so that, when the hinged connection is engaged, the spring 112 provides resistance to forward movement of the user's torso and urges the user's torso back into alignment with the lower body of the user, and when the hinged connection is disengaged, it provides no resistance to forward movement of the user's torso. It is preferable that the upper body engaging portion 104 is substantially devoid of material in the front in the abdominal and pelvic areas that might restrict movement of or access to the abdominal and pelvic areas.

FIGS. 10 to 17 illustrate the preferred embodiment of hinge assembly 108 in greater detail. As shown, torsion spring 112 is mounted within hinge assembly 108. An anchor block 124 is attached to the lower end of upper arm 114. A main body 126 is connected to the upper end of lower arm 116 of the hinge assembly 108, and rotatable via a releasable latching anchor 128 as will be explained in further detail below. A central screw 130 extends through body 126 through spring 112 and also provides a pivot axis for hinge assembly 108, so that upper arm 114 and lower arm 116 may pivot with respect to each other, about the axis of the central screw.

The TAO 100 provides the patient with sufficient force to hold himself more erect, by providing a lifting force at the chest which is created by the torsion springs 112 contained in the mechanical hip joints 108. For the TAO 100 to perform as intended, selection of the spring characteristics is critical in order to provide the specific amount of counterbalance required to match the specific patient's torso weight, physical size, and muscle capability. Selection of the spring will be described in more detail below, but when executed properly, this selection of spring characteristics allows the patient 102 the freedom to bend at the waist as shown in FIGS. 2, 5, and 8, and return to an upright standing position with minimal effort. The TAO 100 is configured so that the patient 102 generally will not bend beyond a safe angle. Such movement is restricted by the hip joints 108 and torsion springs 112 contained therein. As the patient 102 bends forward, the force exerted by the torsion springs 112 increases to the point that the patient reaches a maximum bending allowance. The Lean Angle (θ) (FIGS. 2, 5 and 8) is always less than 90 degrees, thereby preventing the patient 102 from comfortably assuming a normal upright seated position without disengaging the hip joints 108.

Figure 11:
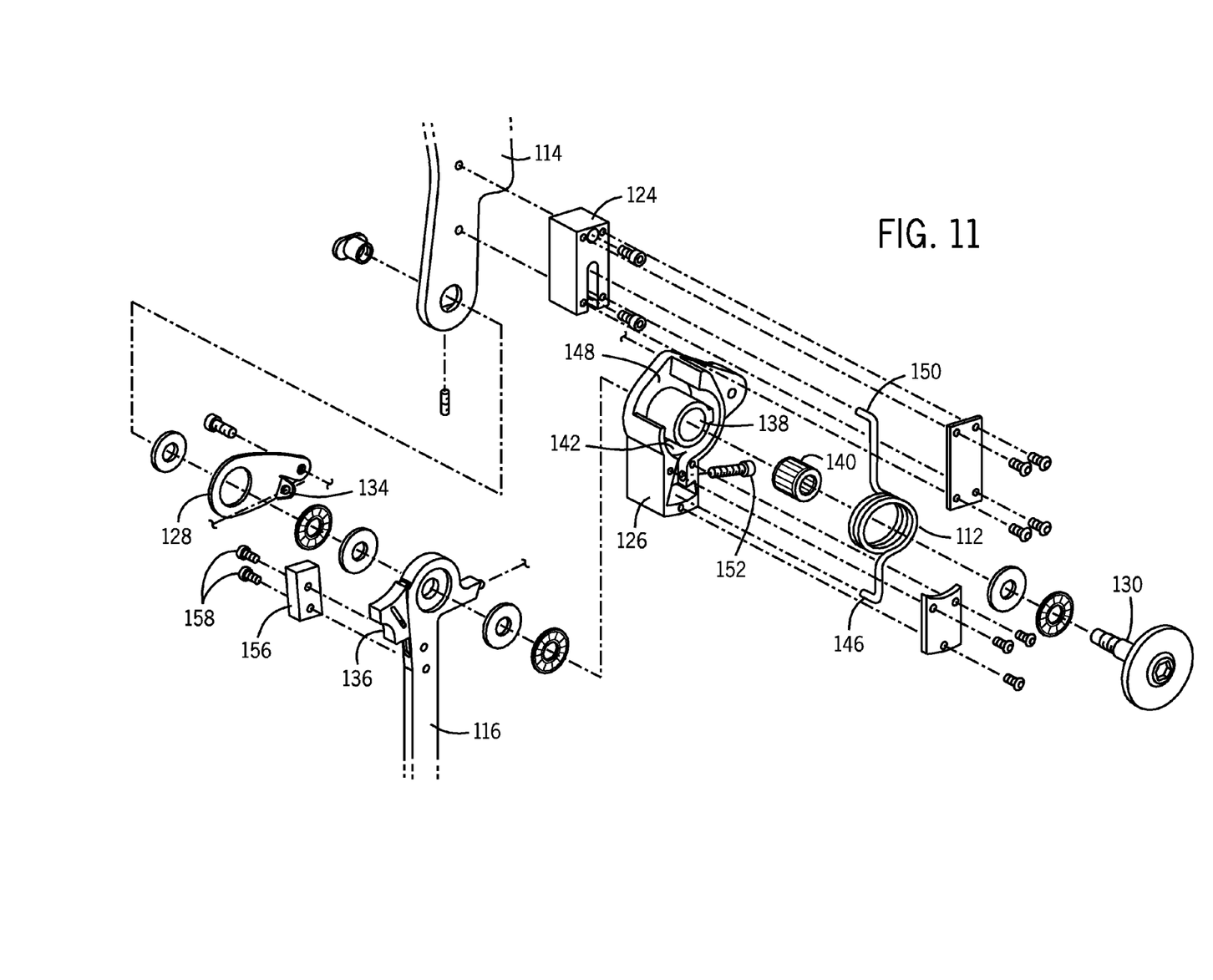
FIG. 11 is an exploded isometric view of the hip joint shown in FIG. 10
Figure 12:
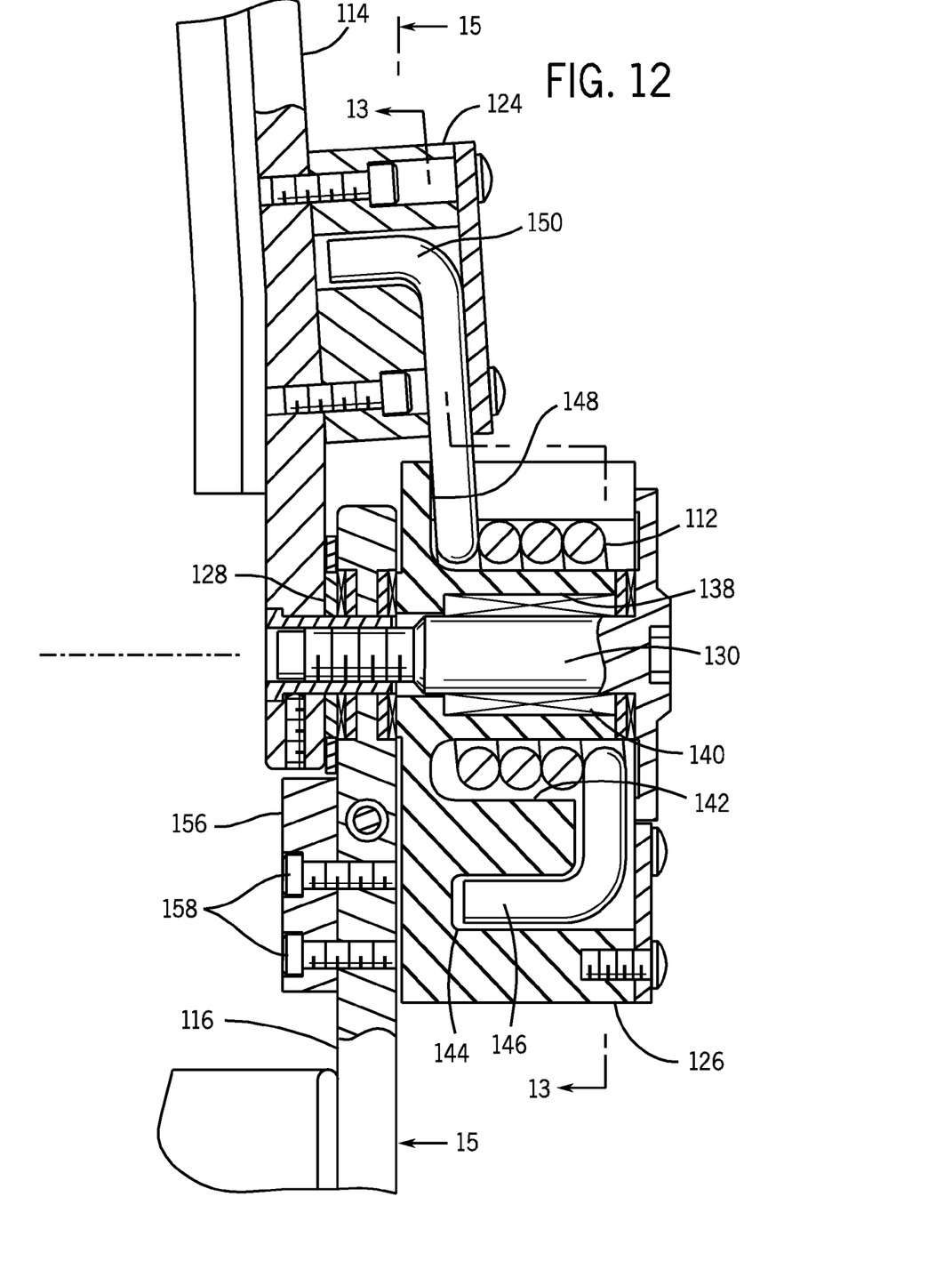
FIG. 12 is a cross-sectional view of the hip joint of the orthotic device shown in FIG. 10, taken along line 12-12 of FIG. 10.
Figure 13:
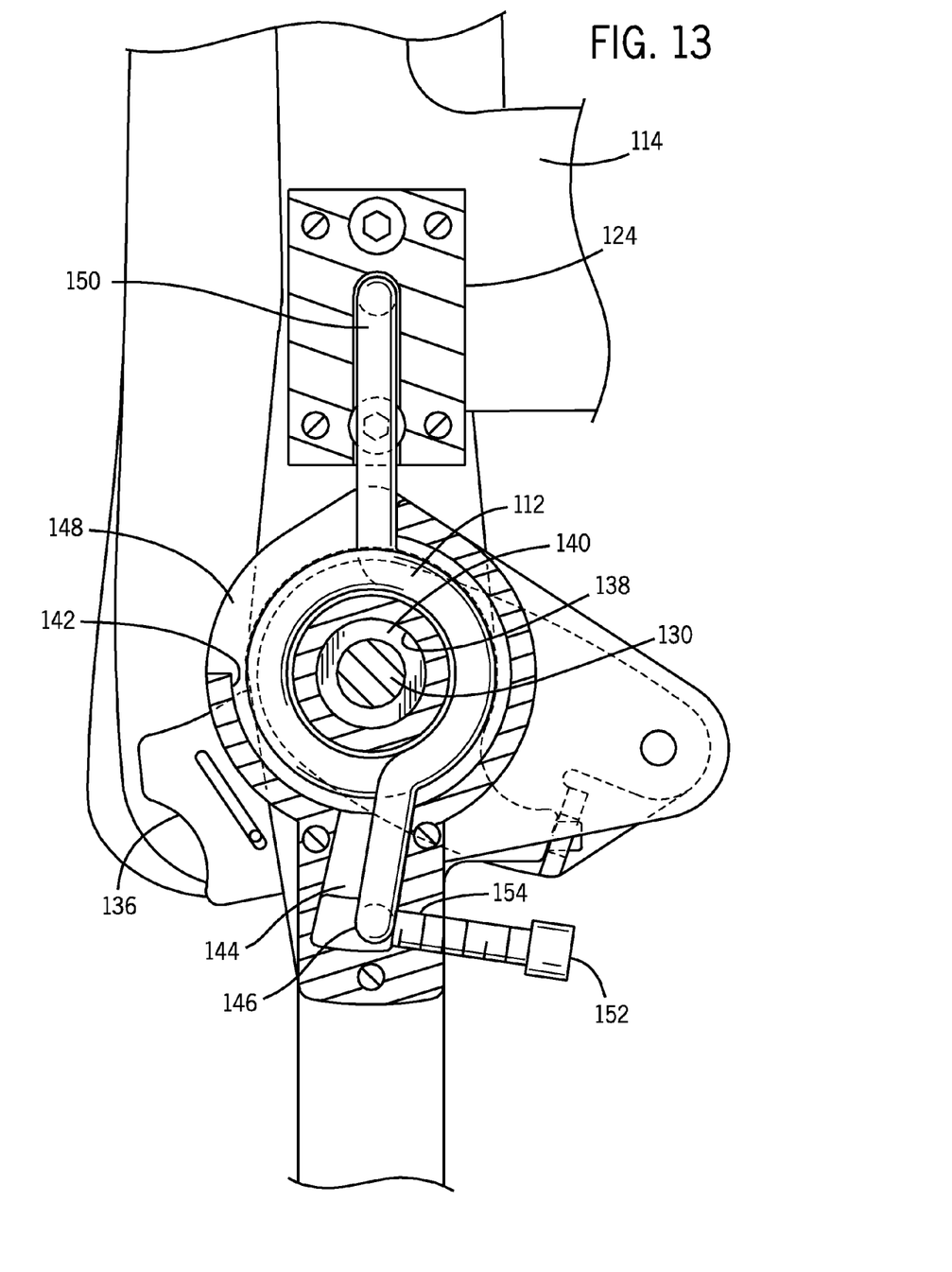
FIG. 13 is a cross-sectional view of the hip joint shown in FIG. 12, taken along line 13-13 of FIG. 12.
Figure 14:
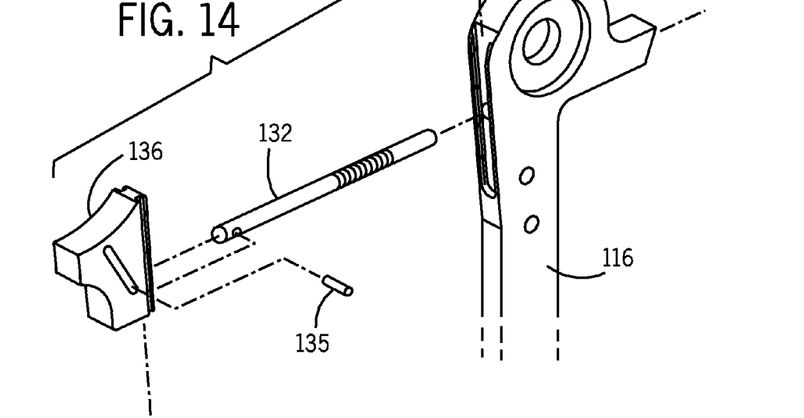
FIG. 14 is an exploded isometric view of certain parts of the hip joint shown in FIG. 10, relating to a locking mechanism.

FIGS. 11 to 13 illustrate main body 126. Main body 126 includes an opening 138 for receiving central screw 130 and a bearing 140 to allow rotation of the body about the screw. It is anticipated that other suitable bearings, bushings or similar pivot schemes may be used within the scope of the present disclosure and it is not intended to limit the disclosure to any particular rotational bearing or support arrangement.

A recess 142 about the opening 138 permits the insertion and anchoring of spring 112 within body 126. A lower extension 144 (FIG. 13) of recess 142 permits a lower spring arm 146 of spring 112 to be anchored to body 126 while an upper opening 148 in recess 142 permits an upper spring arm 150 of spring 112 to extend outside body 126 with a range of motion, and to engage anchor block 124.

The torsion spring 112 asserts little resistance near the vertical position, so that the TAO 100 only minimally impedes normal walking. However, a fully relaxed spring also has no restorative force, so a small amount of spring preload is desirable to ensure that the patient is held fully erect. For this reason, the TAO 100 incorporates a feature that allows adjustment of the preload of the torsion spring 112. However, the amount of preload is kept to a minimum to minimize pressure on the thigh cuffs 122, as a part of lower body engaging portion 106, when walking. As shown best in FIG. 13, a preload adjustment screw 152 is engaged into an opening 154 in body 126 and extends into lower extension 144. Preload screw 152 bears upon the lower arm 146 of spring 112. Lower extension 144 is configured with a space 144a to permit some movement of the lower arm 146 in response to pressure from the preload screw 152. Moving the lower arm 146 of spring 112 by pressing against it with the preload screw 152 serves to preload the spring with some tension so that, with the locking pin 132 engaged, there will be immediate resistance to forward movement of upper arm 114. This preload of spring 112 serves to provide a quicker response and halting of a forward collapse of the user's trunk.

Alternatively, a main body may be configured without a means for providing a preload to spring 112. With the exception of the preload screw provisions, such a main body without preload would otherwise be similarly configured to main body 126.

Selection of the properties of torsion spring 112 begins as shown in FIGS. 2, 5 and 8 by measuring the patient's effective torso weight and distance from the chest support 118 to the center of the patient's hip joint. In order to do this, the patient is asked to stand with his or her pelvis firmly against a fixed object (preferably a parallel bar typically found in physical therapy facilities). A strap is placed about the patient's chest, and the distance from the strap to the center of the patient's hip joint is measured and recorded as the torso Length (L). An accurate tension weight scale is attached to the strap at the patient's back. The patient is then asked to lean forward at an angle (Angle of Lean θ) of 30 to 40 degrees. A lifting force is then applied to the strap through the scale, at an angle preferably perpendicular to the patient's torso. If the lifting force is applied at an angle other than perpendicular, the angle between the lifting force and the perpendicular is designated as α. Assuming α is zero, then the three measurements needed to size the torsion spring are: Torso Length (L), Angle of Lean (θ), and Lifting Force (P).

The patient is asked to completely relax and several small lifts are performed to determine the force required to achieve equilibrium. Once equilibrium is reached, the Angle of Lean θ is measured with a goniometer or arthrometer, along with the Lifting Force P shown on the tension scale, and both are recorded.

The torque (T) required to lift the patient's dead weight is calculated as follows, usually expressed in in-lbs:

$$T = P * \cos(\alpha) * L$$

Assuming α is zero, the above equation simplifies to $$T = P * L$$

The spring rate (R), expressed in in-lbs per degree, is then calculated by dividing torque T by the number of degrees of Angle of Lean θ, as follows:

$$R = T/\theta$$

The above can also be stated another way: the effect of gravity on a leaning torso varies with the sine of the Lean Angle (θ). As can be seen in FIGS. 2, 5 and 8, the force of gravity on a leaning torso is shown as the Weight of the Torso $W_T$. The force to be opposed by the spring, then, is $W_T * \sin(\theta)$.

Figure 19:
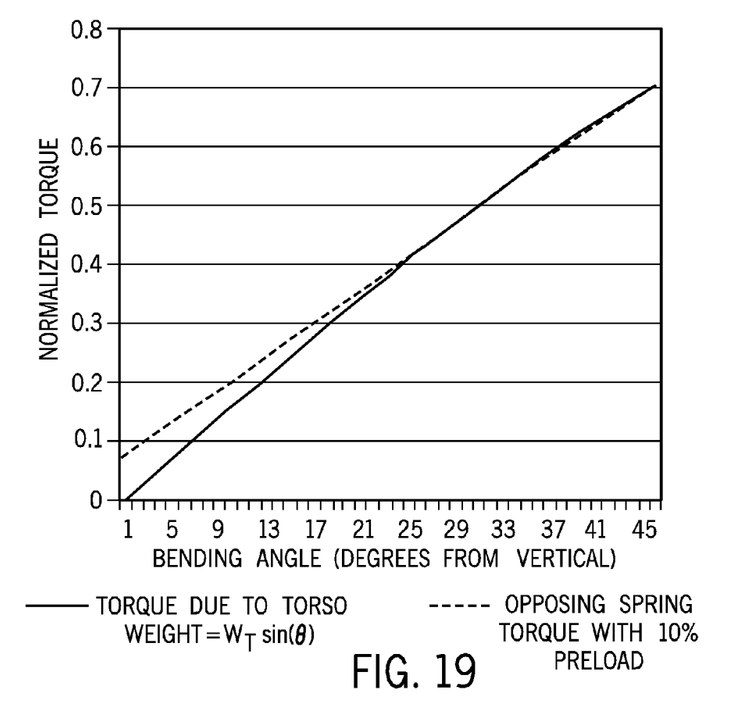
FIG. 19 is a graph illustrating how a torsion spring with constant spring rate and a particular preload can approximate the sine function within a certain range.

Within limited ranges of operation, many torsion springs exhibit a relatively linear spring rate, such that the spring rate R remains somewhat constant throughout the operating range. For the purposes of the TAO 100, the maximum operating range is approximately 45 degrees or less for camptocormia patients and this is typically within the linear region of the spring rate of a torsion spring. While, as stated above, the effect of gravity on a leaning torso actually tends to vary with the sine of the Lean Angle (θ), the normalized curves of FIG. 19 show that, within a 45 degree range, a torsion spring with a constant spring rate and approximately 10% preload provides a reasonable approximation of the sine curve, thus achieving counterbalance.

The strategy for spring selection described herein is but one example of a spring selection strategy. The optimum combination of spring rate and preload depends on the physiology and capability of the individual patient and is ultimately determined on a patient by patient basis.

The present disclosure describes a torsion coil spring 112 to provide the counterbalancing force, but other types could be used. Examples are spiral-wound torsion springs and torsion bars. Other types of restorative devices could also be used. Examples are spring struts, spring loaded cam followers, or even motorized actuators.

Figure 15:
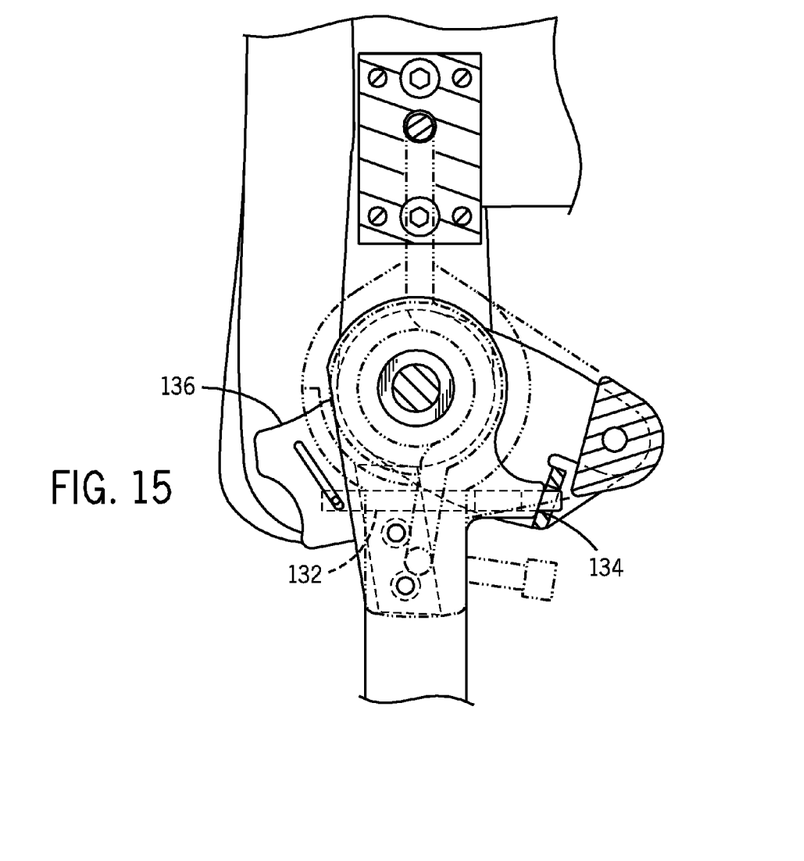
FIG. 15 is a cross-sectional view of the hip joint shown in FIG. 13, taken along line 15-15 of FIG. 12.
Figure 16:
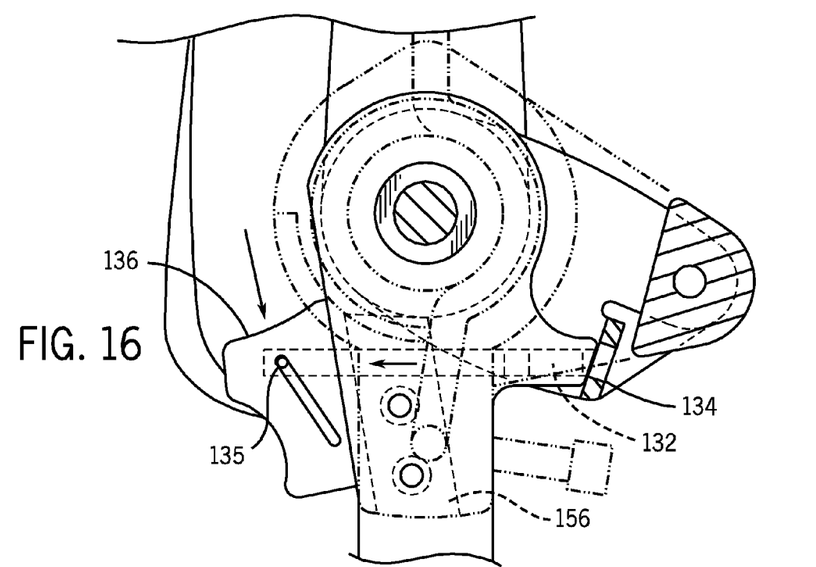
FIG. 16 is a cross-sectional view similar to FIG. 15, but showing the hip joint lock in a different position.
Figure 17:
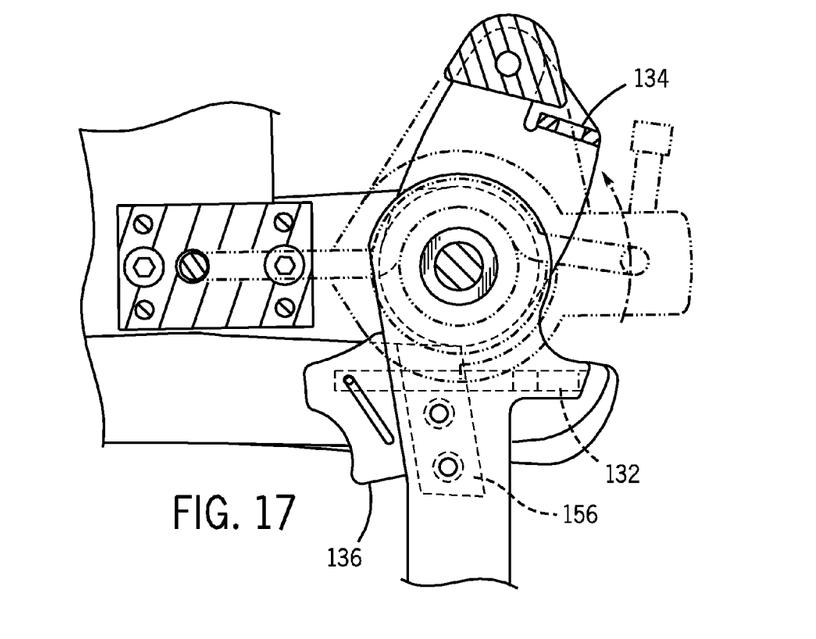
FIG. 17 is a cross-sectional view similar to FIGS. 15 and 16, but showing the hip joint and lock in yet a different position.

In order to comfortably assume a normal upright seated position, such as illustrated in FIGS. 3, 6, and 9, torsion springs 112 must be disengaged from the lower arms 116, which is accomplished by disengaging latching anchor 128. As shown best in FIGS. 10 through 17, in this particular embodiment, which uses a member of the PS200 series or PL200 series from the Center for Orthotics Design, a locking pin 132 is included as part of latching anchor 128 provided with the commercially available hip joint assembly. As shown, the latching anchor 128 is attached to main body 126 such as by a screw 127 (FIG. 11). The latching anchor includes a recess 134 into which pin 132 may be selectively engaged (extended as shown in FIGS. 13 and 15) or disengaged (retracted as shown in FIGS. 16 and 17). This selection is provided by means of a peg 135 which is passed through the outer end of locking pin 132 and mates with a slot formed in a slider 136 for that purpose. The structure of the latching anchor 128 is not described here in detail, as it is part of the basic underlying hip joint, a purchased item as described above. As can be seen in the drawing figures, however, in general terms, sliding the slider 136 downward retracts the locking pin 132 from a recess 134 in releasable latching anchor 128 (FIG. 11), permitting relative movement between the lower arm and the main body 126, and thus free from any influence of the spring 112 (FIG. 17). When the lower arm 116 is brought back into substantial alignment with the upper arm 114, the locking pin 132 again snaps into engagement with the recess 134, and therefore the main body 126, so as to again be controlled by torsion spring 112. Thus is provided the selective engagement or disengagement of the spring assist device of TAO 100. While TAO 100 as illustrated herein is passive and does not assist the patient in transitioning from a seated to standing position, it is anticipated that a powered version could be developed within the scope of the present disclosure which would perform that function. Such an alternative embodiment might include a secondary means of assisting the user in moving from a seated to a standing position to permit the latching anchor 128 to be re-engaged.

In most instances, the spring tension provided by torsion spring 112 alone will act as a forward stop of sorts, as it will be uncomfortable for the patient using the TAO 100 to lean forward beyond about 45 degrees. In the most preferred embodiment, the TAO 100 further includes a positive forward stop, to prevent the hinge assemblies 108 from pivoting beyond 90 degrees, as well as a rearward stop, to prevent the hinge assemblies from pivoting beyond the point where the upper arms 114 and lower arms 116 are substantially aligned with each other.

As described above, when the upper arm 114 is brought back into substantial alignment with the lower arm 116, the locking pin 132 snaps into engagement with the recess 134. This structure provides the function of a rearward stop so as to prevent the upper body engaging portion 104 from pivoting rearwardly beyond being generally in line with the lower body engaging portion 106.

In the embodiment shown in FIGS. 11, 12, 15 and 17, the forward stop function is provided by a stop block 156 affixed to the lower arm 116 at a position so that, when upper arm 114 reaches approximately a 90 degree angle with respect to the lower arm, the upper arm contacts the stop block. That is, the interaction of stop block 156 with upper arm 114 prevents the upper body engaging portion 104 from pivoting forward past approximately ninety degrees with regard to the lower engaging body portion 106. The affixation can be by any suitable means, including by screws 158 as shown in the drawing figures.

Figure 18:
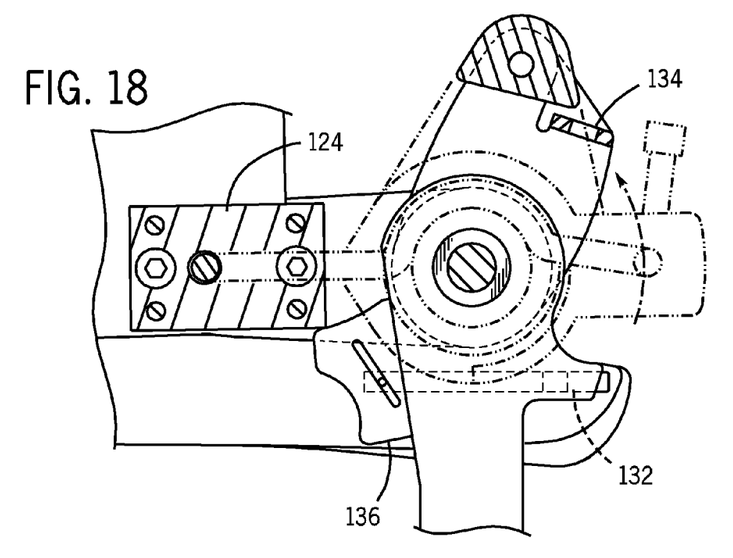
FIG. 18 is a side elevation view, partially in section, of a hip joint constructed according to a different embodiment of the invention.

In an alternative embodiment shown in FIG. 18, anchor block 124 is positioned on upper arm 114 at a position so that the interaction of the anchor block and the slider 136 provides the function of a forward stop so as to prevent the upper body engaging portion 104 from going forward past approximately ninety degrees with regard to the lower body engaging portion 106. In FIG. 18 it can be seen that, with the upper arm 114 at about ninety degrees with respect to lower arm 116, the anchor block 124 hits the slider 136 and can rotate forward no further.

The TAO 100 has been shown in patient testing to provide the assistance needed for patients with advanced camptocormia to stand erect, walk substantially unassisted, bend and reach, and return to a normal standing position. Without the TAO 100, posture may be bent over, characteristic of the syndrome, and mobility may be restricted to a walker. Patients in the early stages of camptocormia will also find relief since they are easily fatigued and can only stand erect for limited periods. For those patients, the torsion springs 112 can be sized to provide less assistance and be less intrusive. Over time, the spring sizes and/or preload can be adjusted as needed.

The TAO 100 is not intended, however, to necessarily be used exclusively to assist camptocormia patients. Others afflicted with an inability to stand erect unassisted may be aided by the device. The main qualifier is an individual's ability to lie on flat surface with the spine straightened and then also be able to stand and bend at the waist without discomfort.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

The invention claimed is:

1. A torso assist orthotic device configured to be worn by a user, the user requiring assistance in holding a torso of the user in a vertical position and returning the user's torso to a vertical position from a forward bent over position, the torso assist orthotic device comprising:
   an upper body engaging portion, including a pair of upper arms, one positioned at each side of the upper body engaging portion;
   a lower body engaging portion, including a pair of lower arms, one positioned at each side of the lower body engaging portion;
   each upper arm rotatably connected to a respective one of the pair of lower arms and forming a hinged connection therewith;
   a spring assist device mounted at and engaging each hinged connection, the spring assist device being selectively disengagable, such that when the spring assist device is engaged, the spring assist device provides resistance to forward movement of the user's torso and urges each upper arm into substantial alignment with the respective lower arm;
   the spring assist device including a self-latching spring engagement/disengagement device; said self-latching spring engagement/disengagement device including a peg, a locking pin and a slider having a slot therein,
   the spring assist device including a forward stop to prevent the upper body engaging portion from going forward past approximately ninety degrees with regard to the lower body engaging portion, and a rearward stop to prevent the upper body engaging portion from going rearward past being generally in line with the lower body engaging portion;
   the spring assist device including a spring selected to counteract the weight of the user's torso so as to aid the return of the user's torso to a vertical position with minimal effort by the user.

2. A torso assist orthotic device of claim 1, the upper body engaging portion being custom molded to the shape of the user's torso.

3. A torso assist orthotic device of claim 1, wherein the spring of each spring assist device is a coil spring engaging the hinged connection with a first portion of the coil spring exerting a spring force on the lower arm and a second portion of the coil spring exerting a spring force on the upper arm.

4. A torso assist orthotic device of claim 3, further comprising a preload adjustment device to tension the coil spring and provide resistance to forward movement of the user's torso.

5. A torso assist orthotic device of claim 1, employing minimal preload only as needed so as to only minimally impede walking by minimizing pressure by the lower body engaging portion when walking.

6. A torso assist orthotic device of claim 1, wherein the hinged connection permits a substantially normal range of motion by the user when the spring assist device is disengaged, such that the user may assume a seated position without the orthopedic device exerting force to bring the user's torso in line with the user's lower body.

7. A torso assist orthotic device of claim 6, wherein the spring assist device automatically reengages when the upper and lower arms become substantially aligned.

8. A torso assist orthotic device of claim 1, wherein the disengagement of the spring assist device comprises the disengagement of the spring assist device from the lower arm.

9. A torso assist orthotic device of claim 1, wherein the lower body engaging portion includes a pair of custom molded thigh cuffs, each connected to a respective one of the lower arms.

10. A torso assist orthotic device of claim 1, wherein the spring assist device further comprises a coil spring with a main coiled spring body, an upper spring arm engaging the upper body engaging portion and a lower spring arm engaging the lower body engaging portion, the coil spring providing a torsional resistance that is substantially directly proportional to angular deflection.

11. A torso assist orthotic device of claim 10, further comprising a preload screw extending through a main body of the spring assist device and configured to selectively contact the lower spring arm of the coil spring to provide a preload force.

* * * * *